(12) United States Patent
Basden

(10) Patent No.: US 8,764,628 B2
(45) Date of Patent: Jul. 1, 2014

(54) DEVICE TO HELP ALLEVIATE REDUCED PENILE ERECTION FIRMNESS

(76) Inventor: William Edward Basden, Clayton, NC (US)

( * ) Notice: Subject to any disclaimer, the term of this patent is extended or adjusted under 35 U.S.C. 154(b) by 504 days.

(21) Appl. No.: 13/017,634

(22) Filed: Jan. 31, 2011

(65) Prior Publication Data

US 2012/0197074 A1 Aug. 2, 2012

(51) Int. Cl.
*A61F 5/41* (2006.01)
(52) U.S. Cl.
CPC .............. *A61F 5/41* (2013.01); *A61F 2005/411* (2013.01)
USPC .......................................................... 600/39
(58) Field of Classification Search
USPC ................................................. 600/38, 39, 41
See application file for complete search history.

(56) References Cited

U.S. PATENT DOCUMENTS

| 4,440,183 | A | * | 4/1984 | Miller | 600/41 |
| 5,085,209 | A | * | 2/1992 | Gottschalk | 600/41 |
| 6,579,229 | B1 | * | 6/2003 | Nan | 600/38 |

* cited by examiner

*Primary Examiner* — Christine Matthews

(57) ABSTRACT

A device to help alleviate any reduced penile erection firmness may include a plurality of strands, each having a first end, a first keeper for gathering the first end of each of the plurality of strands, and a first loop operably coupled to the first keeper. A method to help alleviate any reduced penile erection firmness may include fitting a pair of strands around a user's scrotum, the pair of strands having first ends gathered by a first keeper and second ends gathered by a second keeper, moving one of the pair of strands upwards towards the base of the user's penis, so that the one of the pair of strands is situated at the base of the user's penis, pulling the first keeper and the second keeper over the top of the user's penis; and interlocking the first keeper and the second keeper over the top of the user's penis.

1 Claim, 3 Drawing Sheets

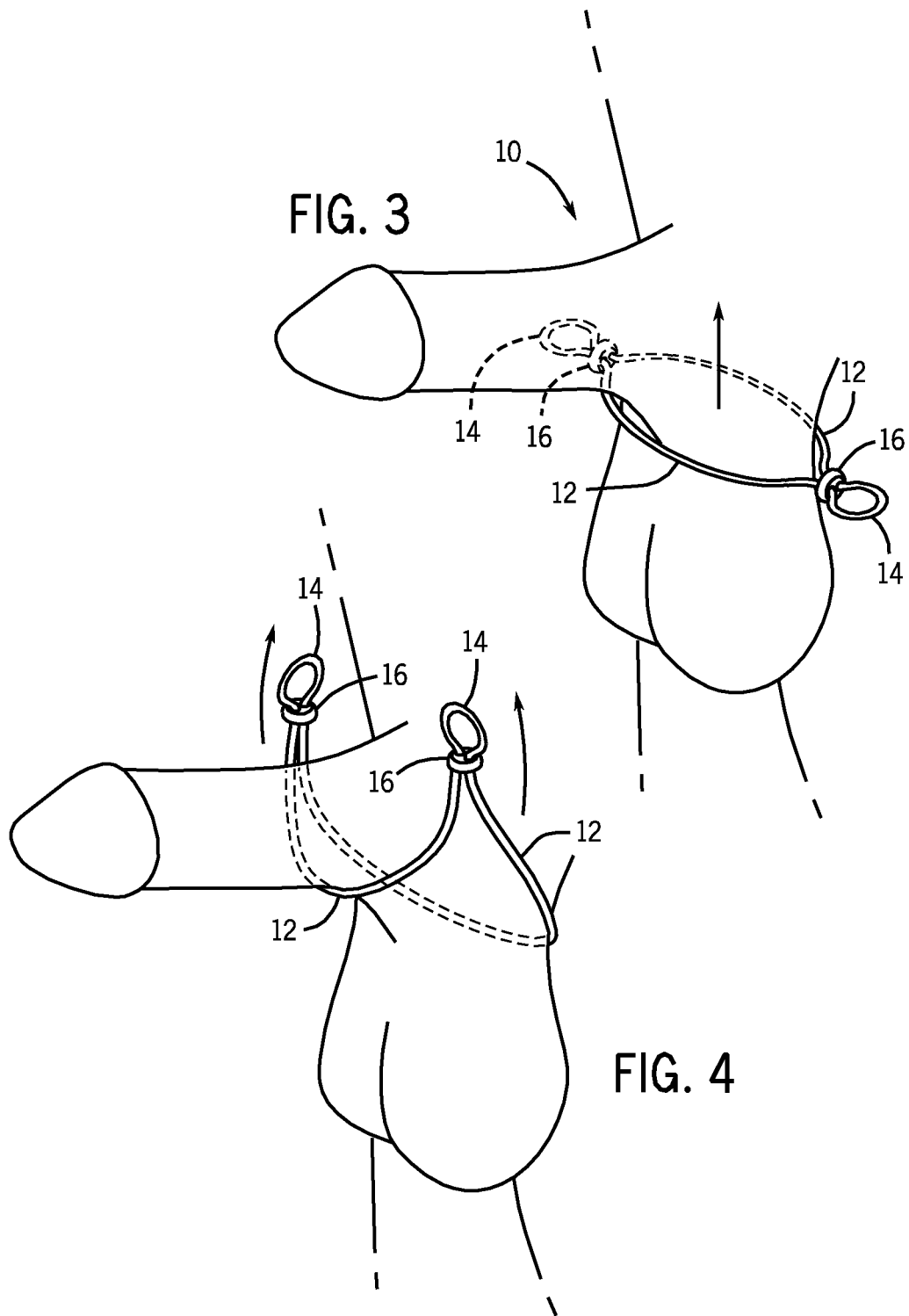

DEVICE TO HELP ALLEVIATE REDUCED PENILE ERECTION FIRMNESS

BACKGROUND OF THE INVENTION

The present invention generally relates to a device for alleviating erectile dysfunction, and more particularly relates to a device that may concurrently and separately encircles the scrotum, testicles, and penis of a user to help alleviate any reduced penile erection firmness.

Erectile dysfunction is a sexual dysfunction typically characterized by an inability to develop or maintain a penile erection. Erectile dysfunction may be caused by many reasons including ageing. Due to the graying of the population here in the United States as well as many other countries, erectile dysfunction as caused by ageing may become a growing health problem.

As can be seen, there is a need for a device for alleviating erectile dysfunction.

SUMMARY OF THE INVENTION

In one aspect of the present invention, a device comprises a plurality of strands, each having a first end; a first keeper for gathering the first end of each of the plurality of strands; and a first loop operably coupled to the first keeper.

In another aspect of the present invention, a method comprises fitting a pair of strands around a user's scrotum, the pair of strands having first ends gathered by a first keeper and second ends gathered by a second keeper; moving one of the pair of strands upwards towards the base of the user's penis, so that the one of the pair of strands is situated at the base of the user's penis; pulling the first keeper and the second keeper over the top of the user's penis; and interlocking the first keeper and the second keeper over the top of the user's penis.

These and other features, aspects and advantages of the present invention will become better understood with reference to the following drawings, description and claims.

BRIEF DESCRIPTION OF THE DRAWINGS

FIG. 3 shows a perspective view showing the first step in applying the device of FIG. 1 to a user;

FIG. 4 shows a perspective view showing the second step in applying the device of FIG. 1 to a user;

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provides a device which may help alleviate reduced penile erection firmness by concurrently and separately encircling the scrotum, testicles, and penis of a user in order to support and sustain a penile erection.

Figure 1:
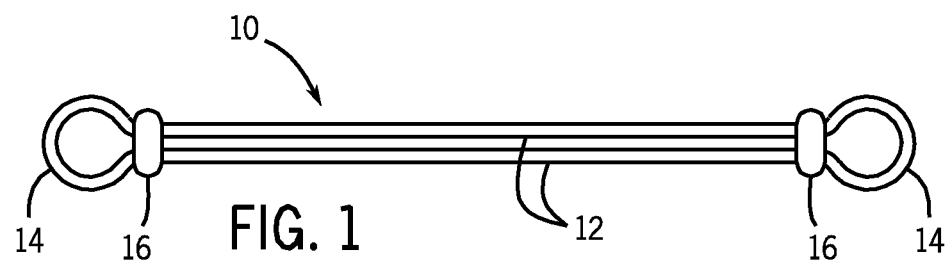
FIG. 1 shows a plan view of a device for alleviating erectile dysfunction in accordance with a first embodiment of the present invention.

With reference to FIG. 1, the device 10 for alleviating reduced penile erection firmness, such as due to erectile dysfunction, may include a plurality of strands 12 that are situated in parallel with one another. A first keeper 16 may gather the first ends of each of the plurality of strands 12, while a second keeper 16 may gather the second ends of the plurality of strands 12 opposite the first ends of the plurality of strands 12. Each of the keepers' 16 ends may be operably coupled to a loop 14. The keepers 16 and the loops 14 may function as interlocking fasteners when the device 10 is in use, and may support compression tension for the strands 12.

In an exemplary embodiment of the present invention, the plurality of strands 12 may include a pair of strands made of non-toxic and resilient material, while the keepers 16 and the loops 14 may be made of plastic. Alternatively, the device 10 may be made of any suitable material or combination of materials. In addition, the plurality of strands 12 may include four strands, six strands, or any other set of even-numbered strands. Further, the device 10 may have approximate dimensions of about 50 millimeters (mm) in length, about 15 mm in width, and about 15 mm in height, having strand 12 diameters of about 1 to 3 mm, and having an approximate weight of about 2 to 5 grams. The device 10 may also be produced with any other set of appropriate dimensions as deemed appropriate for enhanced fit, tension and/or performance capabilities.

Figure 2:
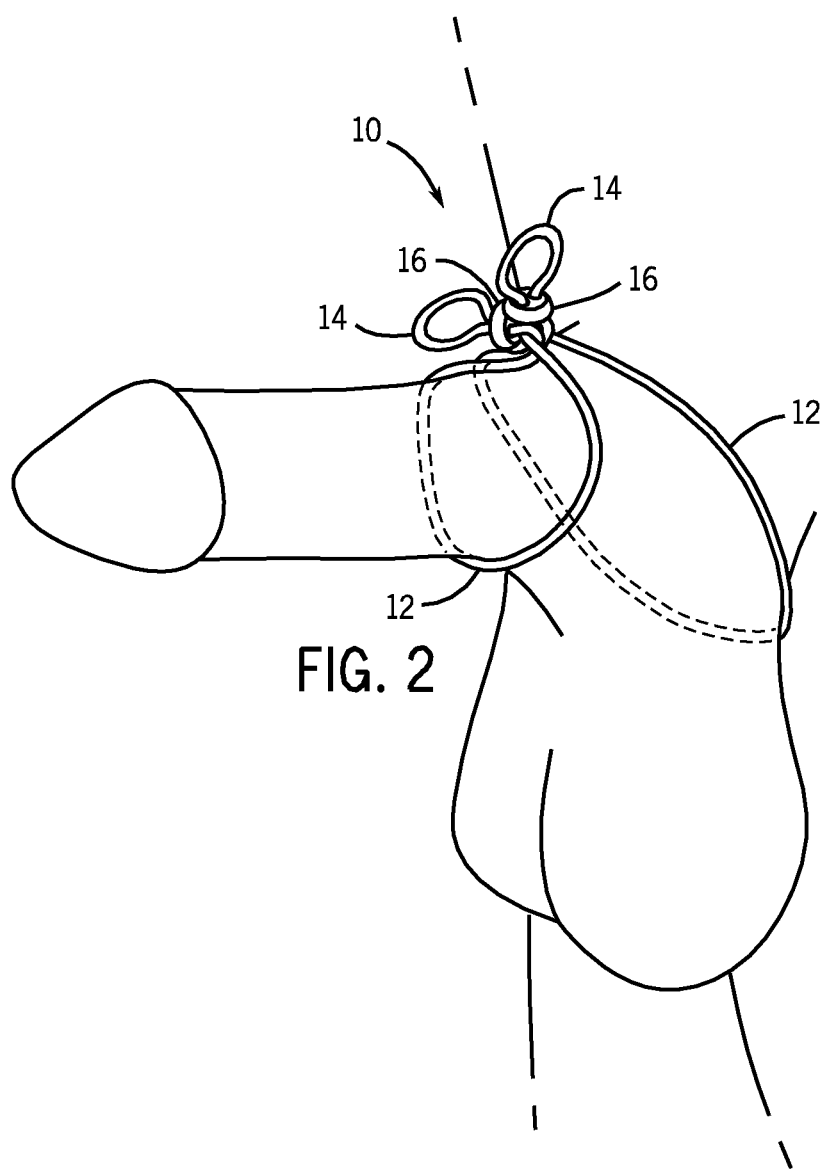
FIG. 2 shows a perspective view of the device of FIG. 1 in use.

With reference to FIG. 2, the device 10 may be used to support and sustain a penile erection. As shown in FIG. 2, when the device 10 has been completely applied to a user, one of the strands 12 may be situated around the base of the user's penis while another one of the strands 12 may be situated around the rear of the user's scrotums. Meanwhile, the pair of strands 12 may be situated at the top of the user's penis, where the keepers 16 and the loops 14 may interlock to secure the device 10 to the user and to support compression tension for the strands 12. When the device 10 has been completely applied by a user, the strands 12 may provide compression tension surrounding the base of the penis to lessen penile vein leakage, and may function externally to promote and sustain penile erection firmness without blocking the penis' internal blood supply.

With reference to FIG. 3, at the first step of applying the device 10 to a user, the pair of strands 12 may be separated for receiving the user's scrotum, starting from the bottom of the scrotum, between the strands 12, and pulling the device 10 upwards on the scrotum towards the penis.

With reference to FIG. 4, at the second step of applying the device 10 to a user, the loops 14 may be pulled upwards, thus causing one of the strands 12 to lift the base of the user's penis. Thus, the strand 12 disposed at the underside base of the user's penis may help to keep the penis erect.

Figure 5:
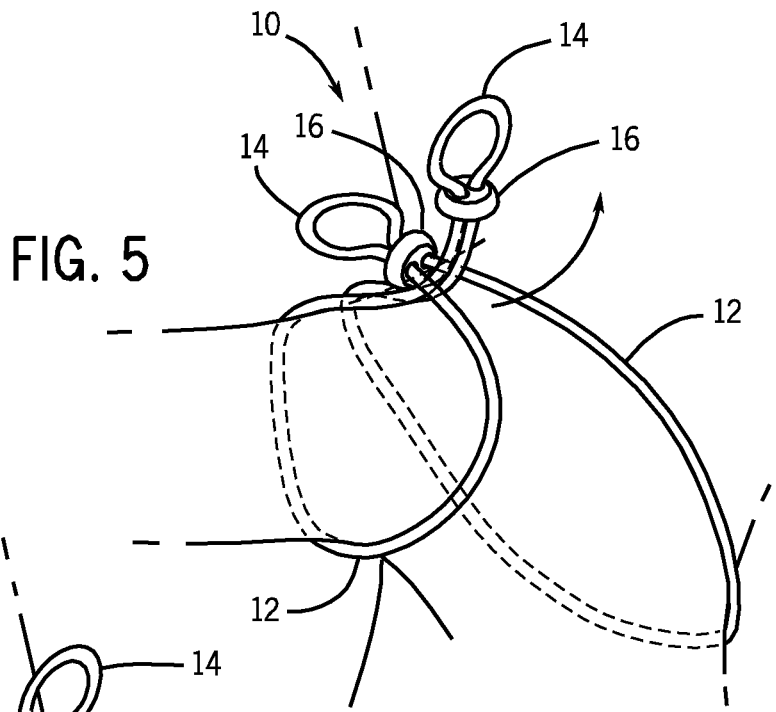
FIG. 5 shows a detailed perspective view showing the third step in applying the device of FIG. 1 to a user.

With reference to FIG. 5, at the third step of applying the device 10 to a user, one of the loops 14 and its corresponding keeper 16 may be looped between the pair of strands 12 at the top of the penis, in order to secure the device 10 to the user and to interlock the loops and the keepers 16.

Figure 6:
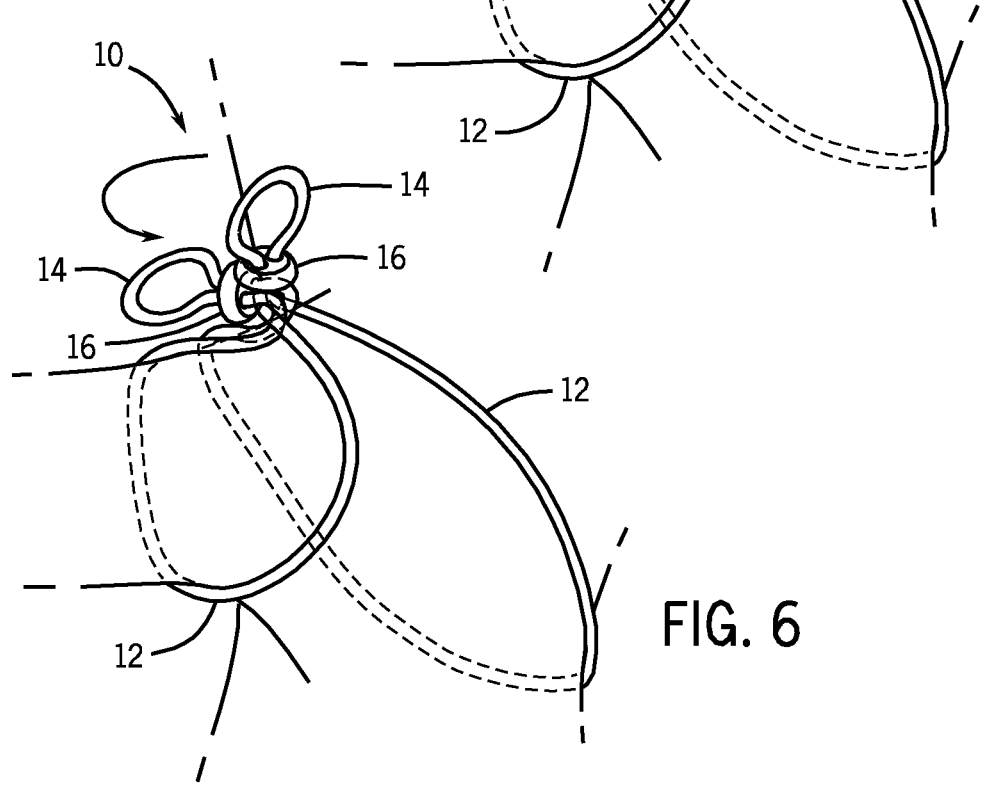
FIG. 6 shows a detailed perspective view showing the forth and final step in applying the device of FIG. 1 to a user.

With reference to FIG. 6, once one of the loops 14 and its corresponding keeper 16 has been looped between the pair of strands 12, the other one of the loops 14 and its corresponding keeper 16 may also be looped between the pair of strands 12, further securing the device 10 to the user. Such double interlocking of the keepers 16 may be optional and may not be required to secure the device 10 depending on the geometrical shape of the keepers 16 and the tautness and the proximity of the strands 12 in relation to each other.

In alternative embodiments of the present invention, the device 10 may be applied to a male genital area in various configurations other than the configurations detailed in FIGS. 2-6.

Figure 7:
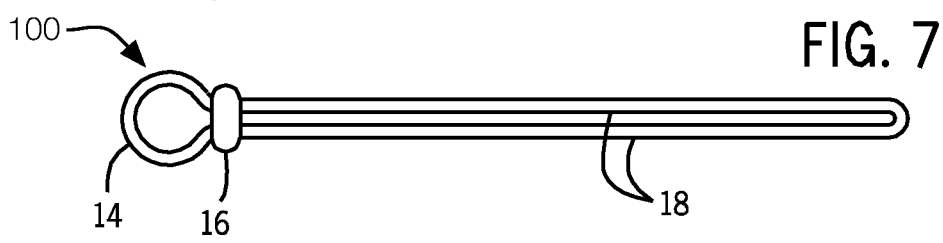
FIG. 7 shows a plan view of a device for alleviating erectile dysfunction in accordance with a second embodiment of the present invention.

With reference to FIG. 7, in accordance with an alternate embodiment of the present invention, an alternate device 100 for alleviating erectile dysfunction may include a pair of strands 18 which may be formed from a length of material that is bent to form a U-shape having a pair of strands 18 situated in parallel. The ends of the pair of strands 18 may be gathered by a keeper 16, and a loop 14 may be operably coupled to the keeper.

It should be understood, of course, that the foregoing relates to exemplary embodiments of the invention and that modifications may be made without departing from the spirit and scope of the invention as set forth in the following claims.

What is claimed is:

1. A method for alleviating reduced penile erection firmness, the method comprising:
   providing a device, the device comprising:
   a first strand that defines a medial portion that is wrapped around a rear facing portion of the scrotum when the device is installed on a patient;
   a second strand that is positioned on a front portion of the scrotum when the device is installed on a patient;
   a first keeper defined on respective first ends of the first strand and the second strand; and
   a second keeper defined on respective second ends of the first strand and the second strand, such that the first strand and the second strand define a space therebetween that receives the scrotum when the device is installed on the patient;
   extending the first strand such that the medial portion engages the rear facing portion of the patient's scrotum and the first and second ends of the first strand are above the patient's penis;
   extending the second strand such that a portion engages on the front portion of the scrotum and the first and second ends of the second strand are above the patient's penis; and
   interlocking the first and second keepers into engagement about a top portion of the penis to thereby secure the device to the patient.

* * * * *